US012790423B2

(12) United States Patent
Mentak

(10) Patent No.: US 12,790,423 B2
(45) Date of Patent: Nov. 10, 2026

(54) POLYMERS AND METHODS FOR OPHTHALMIC APPLICATIONS

(71) Applicant: Key Medical Technologies, Inc., San Ramon, CA (US)

(72) Inventor: Khalid Mentak, San Ramon, CA (US)

(73) Assignee: Key Medical Technologies, Inc., San Ramo (CA)

( * ) Notice: Subject to any disclaimer, the term of this patent is extended or adjusted under 35 U.S.C. 154(b) by 0 days.

(21) Appl. No.: 17/726,267

(22) Filed: Apr. 21, 2022

(65) Prior Publication Data

US 2022/0242983 A1 Aug. 4, 2022

Related U.S. Application Data

(63) Continuation of application No. 17/365,256, filed on Jul. 1, 2021, which is a continuation of application No. 16/166,745, filed on Oct. 22, 2018, now Pat. No. 11,053,335, which is a continuation of application No. 14/517,022, filed on Oct. 17, 2014, now Pat. No. 10,106,637.

(51) Int. Cl.

| | |
|---|---|
| ***C08F 220/18*** | (2006.01) |
| ***A61L 27/16*** | (2006.01) |
| ***C08F 2/50*** | (2006.01) |
| ***C08F 212/32*** | (2006.01) |
| ***C08F 216/14*** | (2006.01) |
| ***C08F 220/20*** | (2006.01) |
| ***C08F 220/26*** | (2006.01) |
| ***C08F 220/30*** | (2006.01) |
| ***C08F 220/68*** | (2006.01) |
| ***C08F 226/12*** | (2006.01) |
| ***C08K 5/3475*** | (2006.01) |
| ***G02B 1/04*** | (2006.01) |
| *A61F 2/16* | (2006.01) |
| *C08F 12/32* | (2006.01) |
| *C08F 16/14* | (2006.01) |
| *C08F 20/26* | (2006.01) |
| *C08F 20/28* | (2006.01) |
| *C08F 26/12* | (2006.01) |
| *C08F 32/08* | (2006.01) |
| *C08F 220/28* | (2006.01) |
| *C08F 232/08* | (2006.01) |

(52) U.S. Cl.

CPC ........ *C08F 220/1807* (2020.02); *A61L 27/16* (2013.01); *C08F 2/50* (2013.01); *C08F 212/32* (2013.01); *C08F 216/14* (2013.01); *C08F 220/20* (2013.01); *C08F 220/26* (2013.01); *C08F 220/301* (2020.02); *C08F 220/68* (2013.01); *C08F 226/12* (2013.01); *C08K 5/3475* (2013.01); *G02B 1/043* (2013.01); *A61F 2/16* (2013.01); *A61F 2002/16965* (2015.04); *A61L 2430/14* (2013.01); *A61L 2430/16* (2013.01); *C08F 12/32* (2013.01); *C08F 16/14* (2013.01); *C08F 20/26* (2013.01); *C08F 20/28* (2013.01); *C08F 26/12* (2013.01); *C08F 32/08* (2013.01); *C08F 220/282* (2020.02); *C08F 220/285* (2020.02); *C08F 220/286* (2020.02); *C08F 232/08* (2013.01); *G02B 1/041* (2013.01)

(58) Field of Classification Search

CPC ........... A61L 27/16; A61L 2002/16965; C08F 220/1806; C08F 220/1807; C08F 220/20; G02B 1/041; G02B 1/043

See application file for complete search history.

(56) References Cited

U.S. PATENT DOCUMENTS

| | | | | |
|---|---|---|---|---|
| 4,808,182 | A | 2/1989 | Barrett | |
| 5,147,394 | A | 9/1992 | Siepser | |
| 5,480,950 | A | 1/1996 | Wang et al. | |
| 5,693,095 | A * | 12/1997 | Freeman | G02B 1/043 351/159.33 |
| 5,810,833 | A | 9/1998 | Brady et al. | |
| 6,281,319 | B1 * | 8/2001 | Mentak | G02B 1/043 526/323.2 |
| 6,329,485 | B1 | 12/2001 | Vanderbilt | |
| 7,939,579 | B1 * | 5/2011 | Tapper | C08F 220/56 528/499 |
| 7,988,701 | B2 | 8/2011 | Vaquero et al. | |
| 10,106,637 | B2 | 10/2018 | Mentak | |
| 2002/0049290 | A1 | 4/2002 | Vanderbilt | |
| 2005/0222578 | A1 | 10/2005 | Vaquero | |
| 2007/0060925 | A1 | 3/2007 | Pynson | |
| 2007/0282057 | A1 | 12/2007 | Mentak | |
| 2008/0064821 | A1 | 3/2008 | Mentak et al. | |
| 2009/0093604 | A1 * | 4/2009 | Schlueter | G02B 1/041 623/4.1 |

(Continued)

FOREIGN PATENT DOCUMENTS

JP 2008-523221 A 7/2008

OTHER PUBLICATIONS

Xie, Shuang et al, "Microstructure of Copolymers containing Disperse Red 1 and Methyl Methacrylate" 1994 Macromolecules, 27, 1885-1890. (Year: 1994).

*Primary Examiner* — Joseph S Del Sole

(74) *Attorney, Agent, or Firm* — Husch Blackwell LLP

(57) ABSTRACT

Novel methods and materials particularly useful for ophthalmic applications and to methods for making and using the same are disclosed herein. More particularly, relatively soft, optically transparent, foldable, high refractive index materials particularly suited for use in the production of intraocular lenses, contact lenses, and other ocular implants and to methods for manufacturing and implanting IOLs made therefrom are disclosed.

4 Claims, No Drawings

(56) References Cited

U.S. PATENT DOCUMENTS

| | | | | |
|---|---|---|---|---|
| 2012/0053313 | A1* | 3/2012 | Higgs | C07C 323/12<br>252/182.17 |
| 2012/0309899 | A1* | 12/2012 | Akinay | A61L 27/16<br>525/55 |
| 2013/0231740 | A1* | 9/2013 | Mentak | A61F 2/1624<br>623/6.59 |

* cited by examiner

POLYMERS AND METHODS FOR OPHTHALMIC APPLICATIONS

CROSS-REFERENCE TO RELATED APPLICATIONS

This application is a continuation patent application of U.S. patent application Ser. No. 17/365,256 filed Jul. 1, 2021, which is a continuation patent application of U.S. patent application Ser. No. 16/166,745 filed Oct. 22, 2018, now U.S. Pat. No. 11,053,335, which is a continuation patent application of U.S. patent application Ser. No. 14/517,022 filed Oct. 17, 2014, now U.S. Pat. No. 10,106,637, which are incorporated herein by reference in their entireties.

FIELD

Disclosed herein are novel materials particularly useful for ophthalmic applications and methods for making and using the same. More particularly, relatively soft, optically transparent, foldable, high refractive index materials particularly suited for use in the production of intraocular lenses, contact lenses, and other ocular implants and to methods for manufacturing and using the same are disclosed.

BACKGROUND

Since the 1940's optical devices in the form of intraocular lenses (IOLs) have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lenses was poly(methyl methacrylate) (PMMA), which is a rigid, glassy polymer.

Softer, more flexible IOLs have gained in popularity in recent years due to their ability to be compressed, folded, rolled or otherwise deformed. Such softer IOLs may be deformed prior to insertion thereof through an incision in the cornea of an eye. Following insertion of the IOL in an eye, the IOL returns to its original, pre-folded shape due to the memory characteristics of the soft material. Softer, more flexible IOLs as just described may be implanted into an eye through an incision that is less than 4.0 mm i.e., much smaller than the 5.5 to 8.0 mm incision necessary to implant more rigid IOLs such as those made from PMMA. A larger incision is necessary for more rigid IOLs because the lens must be inserted through an incision in the cornea slightly larger than the diameter of the inflexible IOL optic portion. Accordingly, more rigid IOLs have become less popular in the market since larger incisions have occasionally been found to be associated with an increased incidence of postoperative complications, such as induced astigmatism.

With recent advances in small-incision cataract surgery, increased emphasis has been placed on developing soft, foldable polymer materials suitable for use in artificial IOLs. In general, these materials fall into one of three categories: hydrogels, silicones and low glass transition temperature acrylics.

A further recent advance in IOL implantation is the use of IOL injectors to implant the IOL in the eye. Cf., US 2007/0060925 "Preloaded IOLS Injector and Methods" to Pynson; US 2005/0222578 "IOL Injector" to Vaquero; and U.S. Pat. No. 7,988,701 "Preloaded IOL Injector" to Vaquero et al.; each of which are incorporated by reference herein in their entireties. Unfortunately injector implantation of an IOL generally proceeds more smoothly (i.e., with fewer surgical difficulties) the more rigid and thus generally the more handleable (manageable), the IOL.

Thus, for surgical purposes, a more rigid lens is suggested. Usually this means a less than fully hydrated polymer lens is injected. As is well known, post-implantation hydration of an IOL changes, sometimes unpredictably, the refractive index (RI) of the lens. This subjects the physician and the injectable IOL implantation to uncertainty as to the surgical outcome.

In general, high water content hydrogel materials have relatively low refractive indices, making them less desirable than other materials with respect to minimal incision size. Low refractive index materials require a thicker IOL optic portion to achieve a given refractive power.

Silicone materials may have a higher refractive index than high-water content hydrogels, but tend to unfold too rapidly after being placed in the eye in a folded position. This can be a problem because a rapid unfolding of a folded lens can potentially damage the corneal endothelium and/or rupture the natural lens capsule and associated zonules.

Low glass transition temperature acrylic materials are desirable because they typically have a high refractive index and unfold more slowly and more controllably than silicone materials when inserted into e.g., the lens capsule. Unfortunately, low glass transition temperature acrylic materials, which contain little or no water initially, may absorb pockets of water, in vivo, causing light reflections or "glistenings." Furthermore, it is difficult to achieve ideal folding and unfolding characteristics due to the temperature sensitivity of acrylic polymer memory.

U.S. Pat. No. 5,480,950 issued Jan. 2, 1996 discloses high refractive index hydrogel materials having a hydrated equilibrium water content ("EWC") of at least 57% for use in the manufacture of IOLs. The high refractive index hydrogel materials are cross-linked polymers prepared from mixtures of N-vinylpyrrolidone, 4-vinylpyrimidine and a vinyl pyridine having equilibrium water contents up to 90% and refractive indexes of 1.560 to 1.594 in the dry state. The IOLs as described are not implanted in a hydrated state. Rather, the IOLs are implanted in a dry, folded and elongated state and hydrated in situ. The refractive indexes in the hydrated state as used in the eye are not provided. U.S. Patent Application Publication 2002/0049290 relates to high refractive index (RI) ophthalmic hydrogel materials.

U.S. Pat. No. 5,693,095 issued Dec. 2, 1997 discloses high refractive index, low water content IOL materials. The materials taught in this particular patent are acrylic materials having an elongation of at least 150%. IOLs manufactured from a material having such elongation characteristics will not crack, tear or split when folded. However, such low water content acrylic materials have been found to be less biocompatible than other materials when manufactured into and used as IOL devices.

In the past decade, hydrophobic polymers have been used in IOL manufacturing with some success. The ophthalmic community has accepted this type of polymer as having good physical properties and acceptable biocompatibility in ocular environments. However, current IOLs made from conventional hydrophobic polymers sometimes suffer from poor optical stability in ocular fluids (e.g. glistenings, optical artifacts) and low refractive indices. The formation of unwanted particles and deposits in the bulk of hydrophobic polymers is attributed to uncontrolled water sorption and subsequent phase separation. Conventional homopolymers currently used to produce copolymers with high RIs (>1.51) absorb varying amounts of water in a sporadic fashion, creating phase separation, haze, and glistenings.

Currently, there are no foldable, high RI IOL polymers that resist the formation of glistenings and deposits. Compositions known to resist formation of glistenings require hydration prior to implantation. This limits foldability, incision size, and preloading packaging, which quickly is becoming the method of choice for packaging IOLs. More importantly, there are no IOLs made with polymers with EWC having a value of in the range of about 3% to about 15% by weight. Not wishing to be bound by any theory, it is believed, however, that this family of polymers is more resistive to glistenings. Compositions, polymers, and methods to manufacture glistening-free IOLs with EWC of 5-15% are provided.

An advantage of the compositions and methods disclosed herein is a reduction or elimination in the uncertainty of surgical outcome in the context of a post-implantation hydratable or hydrating IOL polymer, particularly where implantation is accomplished using an IOL injector.

SUMMARY

Disclosed herein is a new family of high RI polymers particularly suitable for, but not limited to, foldable IOL applications. Materials are optically stable in ocular fluids and resist the formation of unwanted optical artifacts. The unusual properties of the copolymers disclosed herein are achieved by incorporating a hydrophilic polymer within a very hydrophobic polymer matrix that allows the copolymer to have a specific EWC in the range of about 3% to about 15% by weight, preferably in the range of about 4% to about 10% by weight. In addition, the limited amount of water that is absorbed is well distributed and well dispersed within the matrix, preventing macrophase separation noted in prior art compositions. The result is an optically clear material with stable optical properties.

It is well understood that such compositions may result in IOLs with dioptric powers that changes upon implantation in the eye. Another aspect disclosed herein is to anticipate empirically the change in dioptic power via measurements of IOL diopter in a hydrated state prior to drying and sterilization for packaging. Thus, in this further aspect, one or more methods for determining the "after implantation" or post-implantation refractive index/diopter of an intraocular lens is disclosed herein. In this method the lens, usually but not always an intraocular lens, after manufacture, is in a substantially dehydrated state so as to be sufficiently handleable to be implanted into the eye through an incision in the cornea e.g., by means of an IOL injector. That lens after manufacture is hydrated by e.g., soaking it in saline solution e.g., for 24 hours, at room temperature. The diopter of the hydrated lens is measured while the polymer of the lens is in a hydration state similar to the state of hydration it would or will obtain when it is implanted in the eye. The diopter of the IOL is then measured in its hydrated state outside of the eye. The lens then is at least partially dehydrated sufficiently to be sterilized and stored in a substantially dry state to where it is sufficiently handleable to be implanted by means of e.g., an IOL injector. The implanted IOL then is implanted in the eye using an injector through a corneal incision. The implanted, partially dehydrated IOL then hydrates within the eye to where it equilibrates to substantially the same refractive index (and thus diopter) obtained by measurement while it was hydrated prior to implantation. In this practice of the compositions, methods, and polymers disclosed herein, post-implant hydrated IOL refractive index is obtained with approximately 100% certainty while simultaneously obtaining all the advantages of injector or injector-based IOL implantation processes.

In one aspect, disclosed herein is a method of determining post-implantation diopter of a lens pre-implantation comprising the steps of:

- providing an intraocular lens (IOL) comprising a polymer for which the rigidity and refractive index is dependent upon its state of hydration;
- exposing the lens before implantation to a hydrating liquid for a sufficient length of time that the polymer of the IOL hydrates to a state of hydration which is substantially similar to the state of hydration the IOL polymer will obtain post-implantation;
- measuring the diopter value of the substantially hydrated lens; partially dehydrating the lens to enhance its handling characteristics; implanting the partially dehydrated IOL in an eye; and
- permitting the partially dehydrated lens to hydrate in the eye post-implantation to where it obtains the diopter value substantially that of the lens measured pre-implantation.

Novel copolymers particularly adaptable to intraocular lenses ("IOL"), contact lens, and other ophthalmic and optical applications are disclosed herein. IOLs made from compositions and copolymers disclosed herein have a very high refractive index, and may be machined or molded at around room temperature. IOLs disclosed herein may be folded and used to replace a defective natural lens of the eye by insertion through a small incision without the need for further processing or hydration. A particular advantage of the materials, and copolymers disclosed herein is their unusual hybrid character that prevents uncontrolled water sorption.

Foldable ophthalmic lens materials having controllable, uniform, relatively high water content and unexpectedly high refractive indices particularly suited for use as intraocular lenses (IOLs), or other ophthalmic devices such as but not limited to contact lenses, keratoprostheses and corneal rings or inlays, are the primary loci of the compositions, methods, and polymers disclosed herein.

In one embodiment, the disclosure relates to copolymer compositions comprising limited amounts of a monomer having an aromatic monomer and/or a carbazole and/or naphthyl moiety, carbazole, naphthalene, or a naphthyl group and/or a hydrophobic monomer. Carbazole and/or naphthyl moiety monomers are added to the comonomer to increase the refractive index of the copolymer. A monomer having a surface tension generally in the range of 50 dyn/cm or less is used to create a very hydrophobic matrix. A hydrophilic polymer is added to create a hydrophilic phase (in a process described below) for controlled water sorption.

In one embodiment, the disclosure relates to a copolymer comprising a monomer having an aromatic monomer and/or a carbazole and/or naphthyl moiety, carbazole, naphthalene, or a naphthyl group, a first hydrophilic monomer, and second hydrophilic monomer.

In yet another embodiment, the disclosure relates to a copolymer comprising: (a) vinyl naphthalene; (b) 2-(2-ethoxyethoxy)ethyl acrylate; (c) hydroxyethyl acrylate; and (d) a crosslinker.

In still another embodiment, the disclosure relates to a copolymer comprising: (a) a monomer comprising an aromatic, carbazole or naphthyl moiety, carbazole, naphthalene or a naphthyl group and (b) one or more hydrophilic monomers, wherein the one or more hydrophilic monomers are from 68% to 77% by weight of the composition.

In yet another embodiment, the disclosure relates to a copolymer comprising a monomer having an aromatic monomer and/or a carbazole and/or naphthyl moiety, carbazole, naphthalene, or a naphthyl group, and one or more hydrophilic monomers, wherein the composition is at least 60% by weight hydrophilic monomer.

In yet another embodiment, the disclosure relates to a copolymer comprising a monomer having an aromatic monomer and/or a carbazole and/or naphthyl moiety, carbazole, naphthalene, or a naphthyl group, and one or more hydrophilic monomers, wherein the copolymer comprises from 60% to 80% by weight hydrophilic monomer.

In yet another embodiment, the disclosure relates to a copolymer comprising a monomer having an aromatic monomer and/or a carbazole and/or naphthyl moiety, carbazole, naphthalene, or a naphthyl group, and one or more hydrophilic monomers, wherein the copolymer comprises from 70% to 80% by weight hydrophilic monomer.

In yet another embodiment, the disclosure relates to a copolymer comprising a monomer having an aromatic monomer and/or a carbazole and/or naphthyl moiety, carbazole, naphthalene, or a naphthyl group, and one or more hydrophilic monomers, wherein the copolymer comprises from 70% to 75% by weight hydrophilic monomer In yet another embodiment, the disclosure relates to a copolymer comprising a monomer having an aromatic monomer and/or a carbazole and/or naphthyl moiety, carbazole, naphthalene, or a naphthyl group, and one or more hydrophilic monomers, wherein the copolymer comprises from 75% to 80% by weight hydrophilic monomer Accordingly, an advantage of the compositions, polymers, and methods disclosed herein is to provide a biocompatible IOL material having a high refractive index.

Another advantage of the compositions, polymers, and methods disclosed herein is to provide an IOL material having a high refractive index- and controlled water sorption;

Still another advantage of the compositions, polymers, and methods disclosed herein is to allow accurate targeting of the power of the lens in-vivo.

Still another advantage of the compositions, polymers, and methods disclosed herein is to provide an IOL material that is relatively simple to manufacture.

Advantages of the compositions, polymers, and methods disclosed herein are: (1) polymers that are less dysphotopsia; (2) polymers that have excellent biocompatibility; (3) polymers that have good optical clarity; (4) polymers that are resistance to damage, and protection from biocontamination.

Less dysphotopsia. Polymers disclosed herein have higher water content and a lower refractive index relative to hydrophobic acrylic IOLs, minimizing glare, external and internal reflections, and other unwanted visual phenomena.

Excellent biocompatibility. Polymers disclosed herein appear to have a minimal effect on the blood-aqueous barrier and may be excellent options for patients with uveitis and diabetes.

Good optical clarity. Polymers disclosed herein may be more resistant to calcification and may not be associated with the glistenings and inclusions seen in earlier hydrophobic acrylic IOLs.

Resistance to damage during insertion. Polymers disclosed herein are resistant to fold marks and forceps damage.

Protected from biocontamination. Bacteria may be less adhesive to this lens material than to polymethyl methacrylate (PMMA) or hydrophobic acrylic IOLs.

These and other objectives and advantages, some of which are specifically described and others that are not, will become apparent from the detailed description and the claims that follow.

DETAILED DESCRIPTION

All references to the Periodic Table of the Elements refer to the Periodic Table of the Elements published and copyrighted by CRC Press, Inc., 1990. Also, any references to a Group or Groups shall be to the Group or Groups reflected in this Periodic Table of the Elements using the IUPAC system for numbering groups. Unless stated to the contrary, implicit from the context, or customary in the art, all parts and percent are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, product and processing designs, polymers, catalysts, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the weight percent of components within compositions disclosed herein.

The term "about," as used herein in conjunction with a numerical range, modifies that range by extending the boundaries above and below the numerical values set forth. In one embodiment, the term "about" is used herein to modify a numerical value above and below the stated value by a variance of 10%. Therefore, about 50% includes the range of 45%-55%.

As used with respect to a chemical compound, unless specifically indicated otherwise, the singular includes all isomeric forms and vice versa (for example, "hexane", includes all isomers of hexane individually or collectively). The terms "compound" and "complex" are used interchangeably to refer to organic-, inorganic- and organometal compounds. The term, "atom" refers to the smallest constituent of an element regardless of ionic state, that is, whether or not the same bears a charge or partial charge or is bonded to another atom.

"Comprising," "including," "having" and like terms are not intended to exclude the presence of any additional component, step or procedure, whether or not the same is specifically disclosed. In order to avoid any doubt, all processes claimed through use of the term "comprising" may include one or more additional steps, pieces of equipment or component parts, and/or materials unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or," unless stated otherwise, refers to the listed members individually as well as in any combination.

"Composition" and like terms refer to a mixture or blend of two or more components.

"Copolymer" refers to polymers prepared from two different monomers, and polymers prepared from more than two different monomers, e.g., terpolymers, tetrapolymers, etc.

The term "polymer" (and like terms) is a macromolecular compound prepared by reacting (i.e., polymerizing) monomers of the same or different type. "Polymer" includes homopolymers and copolymers.

Materials with high refractive indexes are desirable to allow manufacturers to manufacture thinner IOLs. A thin IOL or thin IOL optic is critical in enabling a surgeon to minimize incision size. Keeping the surgical incision size to a minimum reduces intraoperative trauma and postoperative complications. A thin IOL is also critical for accommodating certain anatomical locations in the eye such as the anterior chamber and the ciliary sulcus. IOLs may be placed in the anterior chamber for increasing visual acuity in both aphakic and phakic eyes and placed in the ciliary sulcus for increasing visual acuity in phakic eyes.

Compositions and polymers disclosed herein have the flexibility required to allow the same to be folded or deformed so that IOLs made therefrom may be introduced into an eye through the smallest possible incision.

In one embodiment, the novel materials are copolymers, trimers, tetramers, etc., comprising at least two monomeric components:

A hydrophobic monomer, and a hydrophilic monomer. In one embodiment, a crosslinker generally is included. In another embodiment, a UV absorber is included.

In one embodiment, the compositions comprise multimers including: a first monomer containing an aromatic, carbazole and/or naphthyl moiety, the aromatic/carbazole/naphthyl moiety monomer being present in the composition at a concentration of at least about 20% and preferably up to about 35-80%.

In another embodiment, the composition further includes a second monomer with a hydrophobic homopolymer, the hydrophobicity being defined as the homopolymer having a surface tension of about 50 dyn/cm or less, the second monomer being present in the copolymer in an amount of at least about 20 weight %, preferably about 50-60 weight %.

In yet another embodiment, the composition then includes at least about 10 weight % of a hydrophilic monomer, preferably about 20-30 weight %. The composition then includes a crosslinking monomer, the crosslinking monomer being present at a concentration in the range up to about 10 weight percent, preferably of about 1 weight % to about 8 weight %.

In still another embodiment, the disclosure relates to compositions comprising a first monomer containing an aromatic, carbazole and/or naphthyl moiety, and one or more hydrophilic monomers. In yet another embodiment, the aromatic/carbazole/naphthyl moiety monomer is present in the composition at a concentration of at least about 20%. In still another embodiment, aromatic/carbazole/naphthyl moiety monomer is present in the composition at a concentration from about 35 to about 80%.

In still another embodiment, the disclosure relates to a copolymer comprising a monomer containing an aromatic, carbazole and/or naphthyl moiety, a first hydrophilic monomer, and a second hydrophilic monomer.

In still another embodiment, the disclosure relates to a copolymer comprising a monomer containing an aromatic, carbazole and/or naphthyl moiety, the aromatic/carbazole/naphthyl moiety monomer being present in the copolymer at a concentration from about 20% by weight to about 30% by weight; and one or more hydrophilic monomers from about 70% by weight to about 80% by weight.

In another embodiment, the copolymer further comprises a crosslinker. In still other embodiments, the copolymer further comprises a UV absorber. In yet another embodiment, the copolymer further comprises an initiator, including but not limited to Azobisisobutyronitrile (AIBN).

In still another embodiment, the disclosure relates to a copolymer comprising a monomer containing an aromatic, carbazole and/or naphthyl moiety, a first hydrophilic monomer, a second hydrophilic monomer, a UV absorber, a crosslinker, and an initiator.

In another embodiment, one or more hydrophilic monomers comprise from about 50% to about 80% by weight of the copolymer, or from about 55% to about 80% by weight of the copolymer or from about 60% to about 80% by weight of the copolymer, or from about 65% to about 80% by weight of the copolymer, or from about 70% to about 80% by weight of the copolymer, or from about 75% to about 80% by weight of the copolymer.

In yet another embodiment, one or more hydrophilic monomers comprise from about 50% to about 75% by weight of the copolymer, or from about 50% to about 70% by weight of the copolymer, or from about 50% to about 65% by weight of the copolymer, or from about 50% to about 65% by weight of the copolymer, or from about 50% to about 55% by weight of the copolymer.

In yet another embodiment, one or more hydrophilic monomers comprise from about 62% to about 80% by weight of the copolymer, or from about 64% to about 80% by weight of the copolymer, or from about 66% to about 80% by weight of the copolymer, or from about 68% to about 80% by weight of the copolymer, or from about 72% to about 80% by weight of the copolymer, or from about 74% to about 80% by weight of the copolymer, or from about 76% to about 80% by weight of the copolymer, or from about 78% to about 80% by weight of the copolymer.

In yet another embodiment, one or more hydrophilic monomers comprise from about 66% to about 78% by weight of the copolymer, or from about 66% to about 76% by weight of the copolymer, or from about 66% to about 74% by weight of the copolymer, or from about 66% to about 72% by weight of the copolymer, or from about 66% to about 70% by weight of the copolymer, or from about 66% to about 68% by weight of the copolymer.

In yet another embodiment, one or more hydrophilic monomers comprise from about 67% to about 78% by weight of the copolymer, or from about 68% to about 78% by weight of the copolymer, or from about 69% to about 78% by weight of the copolymer, or from about 70% to about 78% by weight of the copolymer, or from about 71% to about 78% by weight of the copolymer, or from about 72% to about 78% by weight of the copolymer, or from about 73% to about 78% by weight of the copolymer, or from about 74% to about 78% by weight of the copolymer, or from about 57% to about 78% by weight of the copolymer, or from about 76% to about 78% by weight of the copolymer, or from about 77% to about 78% by weight of the copolymer.

In yet another embodiment, one or more hydrophilic monomers comprise from about 67% to about 75% by weight of the copolymer, or from about 68% to about 75% by weight of the copolymer, or from about 69% to about 75% by weight of the copolymer, or from about 70% to about 75% by weight of the copolymer, or from about 71% to about 75% by weight of the copolymer, or from about 72% to about 75% by weight of the copolymer, or from about 73% to about 75% by weight of the copolymer, or from about 74% to about 75% by weight of the copolymer.

Suitable hydrophilic monomers (i.e., monomers whose homopolymers are hydrophilic in accordance with the compositions, methods, and polymers disclosed herein) include but are not limited to 2-hydroxy-ethylacrylate, 2-hydroxyethylmethacrylate, acrylamide, N-ornithine acrylamide, N-(2-hydroxypropyl)acrylamide, polyethyleneglycol acrylates, polyethyleneglycol methacrylates, N-vinyl pyrolidone, N-phenylacrylamide, dimethylaminopropyl methacrylamide, acrylic acid, benzylmethacrylamide, 4-hydroxybutylmethacrylate, glycerol mono methacrylate, glycerol mono acrylate, 2-sulfoethylmethacrylate, phenoxyethyl acrylate, phenoxy ethyl methacrylate, 2-(2-ethoxyethoxy)ethyl acrylate, 2-(2-ethoxyethoxy)ethyl methacrylate, furfuryl acrylate, furfuryl methacrylate, and methylthioethylacrylamide. Any of the above-referenced hydrophilic monomers can be a first or a second hydrophilic monomer in a composition.

Suitable hydrophobic monomers (i.e., monomers whose homopolymers are hydrophobic in accordance with the compositions, methods, and polymers disclosed herein) include but are not limited to Lauryl methacrylate, Lauryl acrylate, 2-ethylhexyl acrylate, 2-ethylhexyl methacrylate, n-decyl acrylate, n-decyl methacrylate, hexyl acrylate, hexyl methacrylate, stearyl acrylate, stearyl methacrylate, isodecyl acrylate, isodecyl methacrylate, isobornyl acrylate, isobornyl methacrylate, vinyl laurate, vinyl stearate, 1-hexadecyl acrylate, 1-hexadecyl methacrylate, n-myristyl acrylate, n-myristyl methacrylate, n-dodecyl methacrylamide, butyl acrylate, n-butyl methacrylate, isooctyl acrylate, isotridecyl acrylate, isooctyl methacrylate, and isotridecyl methacrylate.

Suitable crosslinkers include for example but are not limited to ethylene glycol dimethacrylate (EGDMDA), diethylene glycol dimethacrylate, triethylene glycol dimethacrylate and poly(ethylene glycol) dimethacrylate wherein ethylene glycol dimethacrylate is preferred. Suitable initiators include for example but are not limited to azobis (isobutyronitrile), 2,2'-azobis(2,4-dimethylvaleronitdle), 2,2'-azobis(methylbutyronitrile), 1,1'-azobis(cyanocyclohexane), di-t-butyl peroxide, dicumyl peroxide, t-butylcumyl peroxide, 2,5-dimethyl-2,5-bis(2-ethylhexanoyl peroxy)hexane, t-butyl peroxyneodecanote, t-butyl peroxy 2-ethylhexanoate, di(4-t-butyl cyclohexyl) peroxydicarbonate, t-butyl peroxypivalate, decanoyl peroxide, lauroyl peroxide, benzoyl peroxide, 2,4-pentanedione peroxide, di(n-propyl) peroxydicarbonate, t-amyl peroxyneodecanoate and t-butyl peroxyacetate wherein 2,2'-azobis(isobutyronitrile) is preferred. Suitable ultraviolet light absorbers include for example but are not limited to beta-(4-benzotriazoyl-3-hydroxyphenoxy)ethyl acrylate, 4-(2-acryloxyethoxy)-2-hydroxybenzophenone, 4-methacryloxy-2-hydroxybenzo-phenone, 2-(2'-methacryloxy-5'-methylphenyl)benzotriazole, 2-(2'-hydroxy-5'-methacryoxyethylphenyl)-2H-benzotriazole, 2-[3'-tert-Butyl-2'-hydroxy-5'-(3"-methacryloyloxypropyl)phenyl]-5-chloro-benzotriazole, 2-(3'-tert-Butyl-5'-[3"-dimethyl-vinyisilylpropoxy)-2'-hydro-xyphenyl]-5-methoxybenzotriazole, 2-(3'-Allyl-2'-hydroxy-5'-methylphenyl)benzotriazole, 2-[3'-tert-Butyl-2'-hydroxy-5'-(3" methacryloyloxypropoxy)phenyl]-5-methoxybenzotriazole, and 2-[3'-tert-Butyl-2'-hydroxy-5'-(3"-methacryloyloxypropoxy)phenyl]-5-chlorobenzotriazole wherein beta-(4-benzotriazoyl-3-hydroxyphen-oxy)ethyl acrylate is the preferred ultraviolet light absorber.

In one embodiment, the crosslinker may present from about 0.1% to about 10% by weight of the composition or from about 0.3% to about 10% by weight of the composition or from about 0.5% to about 10% by weight of the composition or from about 1% to about 10% by weight of the composition or from about 2% to about 10% by weight of the composition or from about 3% to about 10% by weight of the composition or from about 4% to about 10% by weight of the composition or from about 5% to about 10% by weight of the composition or from about 6% to about 10% by weight of the composition.

In one embodiment, a crosslinker may present from about 1% to about 5% by weight of the composition or from about 2% to about 5% by weight of the composition or from about 3% to about 5% by weight of the composition or from about 4% to about 5% by weight of the composition.

A UV absorber optionally may be added to the copolymer compositions. A novel, preferred, UV/blue light absorber, i.e., vinyl anthracene, may be added to the copolymer compositions. Conventional UV absorbers, such as a vinyl benzophenone or a vinyl benzotriazole, also may be used.

In another embodiment, a UV absorber may present from about 0.1% to about 5% by weight of the composition or from about 0.2% to about 5% by weight of the composition or from about 0.4% to about 5% by weight of the composition or from about 0.6% to about 5% by weight of the composition or from about 0.8% to about 5% by weight of the composition or from about 1% to about 5% by weight of the composition or from about 1.5% to about 5% by weight of the composition or from about 2% to about 5% by weight of the composition or from about 3% to about 5% by weight of the composition or from about 4% to about 5% by weight of the composition.

In yet another embodiment, the disclosure relates to a copolymer comprising: (a) a monomer containing an aromatic, carbazole and/or naphthyl moiety present from about 18% to about 28% by weight of the composition, (b) a first hydrophilic monomer present from about 39% to about 49% by weight of the composition, and (c) a second hydrophilic monomer present from about 23% to about 33% by weight of the composition.

In yet another embodiment, the disclosure relates to a copolymer comprising: (a) a monomer containing an aromatic, carbazole and/or naphthyl moiety that is at least about 20% by weight of the copolymer (b) a first hydrophilic monomer that is at least about 40% by weight of the composition, and (c) a second hydrophilic monomer that is at least about 25% by weight of the composition.

In still another embodiment, the disclosure relates to a copolymer comprising: (a) monomer containing an aromatic, carbazole and/or naphthyl moiety, including but not limited to vinyl carbazole, vinyl naphthalene, 2-vinyl naphthalene, and mixtures thereof; (b) a first hydrophilic monomer of 2-(2-ethoxyethoxy)ethyl acrylate, and (c) a second hydrophilic monomer of hydroxyl acrylate. In another embodiment, the copolymer further comprises a UV absorber. In still another embodiment, the copolymer comprise a crosslinker, including but not limited to ethylene glycol dimethacrylate. In still another embodiment, the copolymer comprises an initiator, including but not limited to AIBN.

In still another embodiment, the disclosure relates to a copolymer comprising: (a) 2-vinyl naphthalene, (b) a first hydrophilic monomer that is 2-(2-ethoxyethoxy)ethyl acrylate, (c) a second hydrophilic monomer that is hydroxyl acrylate, (d) a UV absorber, (e) a crosslinker, and (f) an initiator.

In still another embodiment, the disclosure relates to a copolymer comprising: (a) 2-vinyl naphthalene that is at least about 20% by weight of the composition, (b) a first hydrophilic monomer that is 2-(2-ethoxyethoxy)ethyl acrylate that is at least about 40% by weight of the composition, (c) a second hydrophilic monomer that is hydroxyl acrylate that is at least about 25% by weight of the composition, (d) a UV absorber that is at least about 0.5% by weight of the composition, (e) a crosslinker that is at least about 2.5% by weight of the composition, and (f) an initiator that is at least about 0.1% by weight of the composition.

In still another embodiment, the disclosure relates to a copolymer comprising a monomer containing an aromatic, carbazole and/or naphthyl moiety, a first hydrophilic monomer, and a second monomer with a homopolymer having a glass transition temperature (Tg) less than 20° C.

In yet another embodiment, the disclosure relates to a copolymer comprising: (a) a monomer containing an aromatic, carbazole and/or naphthyl moiety present from about 18% to about 28% by weight of the composition, (b) a first hydrophilic monomer present from about 39% to about 49% by weight of the composition, and (c) a second monomer with a homopolymer having a Tg less than 20° C. present from about 23% to about 33% by weight of the composition.

In yet another embodiment, the disclosure relates to a copolymer comprising: (a) a monomer containing an aromatic, carbazole and/or naphthyl moiety that is at least about 20% by weight of the copolymer (b) a first hydrophilic monomer that is at least about 40% by weight of the composition, and (c) a second monomer with a homopolymer having a Tg less than 20° C. that is at least about 25% by weight of the composition.

In one embodiment, a copolymer disclosed herein has an EWC in the range of about 5% to about 15% by weight. In one embodiment, a copolymer disclosed herein has an EWC in the range of about 3% to about 15% by weight. In another embodiment, a copolymer disclosed herein has an EWC in the range of about 4% to about 10% by weight. In another embodiment, a copolymer disclosed herein has an EWC in the range of about 5% to about 10% by weight.

In one embodiment, a copolymer disclosed herein in a dry state has an EWC in the range of about 5% to about 15% by weight. In one embodiment, a copolymer disclosed herein in a dry state has an EWC in the range of about 3% to about 15% by weight. In another embodiment, a copolymer disclosed herein in a dry state has an EWC in the range of about 4% to about 10% by weight. In another embodiment, a copolymer disclosed herein in a dry state has an EWC in the range of about 5% to about 10% by weight.

In another embodiment, the compositions and copolymers disclosed herein can be used to produce IOL's using techniques known in the art. In one embodiment, an IOL is produced using a lathe cutting method. In general, lathe cutting puts the lens material on a rotating mount, while machine cutting instruments sculpt away excess lens material to carve a precision-cut lens. The lenses are then polished and characterized.

In another embodiment, the IOL is produced using a molding technique. In one embodiment, the comonomer solution is injected into a mold, cured at 60° C. for 4 hours and post cured at 100° C. for 4-8 hours. The IOL is demolded and extracted with an appropriate solvent.

In another embodiment, injection molding for contact lenses is performed by heating the lens material to the point of melting, then injecting the liquid lens material into a pre-cut mold. Once the lens material dries, it will solidify in the form of the mold, giving precise shape to the lens. After the lens is removed, extra material may be removed, and the lens will be polished prior to being inspected for quality and characterization.

TABLE 1

Examples 1-9:

| Example | Monomer | Concentration | RI | % EWC | Tg ° C. | ΔD upon hydration |
|---|---|---|---|---|---|---|
| 1 | PEA | 70 | 1.5341 | 7 | 2 | 0.6 |
| | HEA | 27 | | | | |
| | EGDM | 3 | | | | |
| 2 | PEMA | 67 | 1.5401 | 6 | 12 | 0.6 |
| | HEA | 30 | | | | |
| | EGDM | 3 | | | | |
| 3 | PEA | 67 | 1.5441 | 8 | 16 | 0.8 |
| | HEMA | 30 | | | | |
| | EGDM | 3 | | | | |
| 4 | BA | 70 | 1.5241 | 9 | 10 | 1.0 |
| | HEA | 27 | | | | |
| | EGDM | 3 | | | | |
| 5 | POEA | 70 | 1.5201 | 10 | 19 | 1.0 |
| | HEMA | 27 | | | | |
| | EGDM | 3 | | | | |
| 6 | BMA | 60 | 1.5312 | 8 | 18 | 0.8 |
| | HEA | 20 | | | | |
| | LM | 17 | | | | |
| | EGDM | 3 | | | | |
| 7 | VC | 27 | 1.5213 | 6 | 10 | 0.5 |
| | HEA | 20 | | | | |
| | LM | 50 | | | | |
| | EGDM | 3 | | | | |
| 8 | VC | 30 | 1.5422 | 14 | 7 | 0.8 |
| | EHA | 42 | | | | |
| | HEA | 25 | | | | |
| | EGDM | 3 | | | | |
| 9 | VN | 23.4 | 1.5332 | 8 | −2 | 1.2 |
| | EEEA | 44.2 | | | | |
| | HEA | 28.0 | | | | |
| | EGDM | 3.1 | | | | |

0.3% by weight of MEB was used in all copolymer compositions.

PEA: 2-phenylethyl acrylate
PEMA: 2-phenylethyl methacrylate
POEA: Phenoxyethyl acrylate
BA: Benzyl acrylate
BMA: Benzyl methacrylate
VC: vinyl carbazole
VN: vinyl naphthalene
EHA: 2-ethylhexylacrylate
LM: Lauryl methacrylate
HEMA: Hyroxyethylmethacrylate
HEA: Hydroxyethylacrylate
EEEA: 2-(2-ethoxyethoxy)ethyl acrylate
EGDM: ethylene glycol dimethacrylates
MEB: 2-(2'-Methacryloxy-5'methylphenyl)benzotriazole General Preparation Steps for Polymers of Table 1, Example 1-9

The comonomers listed above were mixed in a glass flask using a magnetic stir bar for at least 30 minutes followed by sonication for the times indicated, and then stirring again for another 30 minutes.

We found that sonicating for about 30 minutes at a power setting of 100% on a Branson 5510 provides optically clear materials with adequate optical and physical properties. The monomer solution is degassed with argon and poured in 6 in.×6 in. molds made from glass plates separated by a silicone gasket. The molds were kept at 60° C. for 6 hours and then post-cured in vacuo at 100° C. for 12 hours.

The resulting copolymers are rigid enough to be machined at around room temperature. A unique aspect of the compositions, methods, and polymers disclosed herein is that the refractive index of these materials is so high that lenses are made thin enough to be folded without further processing or hydration.

IOLs are machined from the copolymers to exact diopters. The IOLs are hydrated in distilled water for 3 hours at 50° C. and the diopter measured again in a hydrated state. The value obtained is the actual power of the lens that should be used for labeling purposes.

Alternatively, a mathematical formula relating the diopter of a dry lens to that of the same lens hydrated may be developed from data such as that discussed below and used to label the IOLs.

Empirical Estimation of In-Vivo Lens Diopter

Unlike conventional hydrogel where lens hydration results into a significant decrease in diopter due to a decrease of RI of the polymer upon absorbing water, the lenses disclosed herein exhibit a relatively modest change in diopter upon hydration due to the small amount of water absorbed and a counterbalancing effect of the lens swelling and concomitant steepening of the radius of curvature. Lenses were lathe cut from sheets made from polymer compositions made according to the procedure described previously. Ten (10) lenses were selected for each composition. Table 2 below shows the diopter of 20 D lenses made from polymer examples 1-8 before and after hydration:

TABLE 2

| Examples 1-8: | | | | | | |
|---|---|---|---|---|---|---|
| Example | RI | % EWC | Diopter before hydration (D) | SD* | Diopter after hydration (D) | SD |
| 1 | 1.5341 | 7 | 20.0 | 0.1 | 20.6 | 0.3 |
| 2 | 1.5401 | 6 | 20.0 | 0.2 | 20.6 | 0.3 |
| 3 | 1.5441 | 8 | 20.0 | 0.1 | 20.8 | 0.2 |
| 4 | 1.5241 | 9 | 20.0 | 0.1 | 21.0 | 0.2 |
| 5 | 1.5201 | 10 | 20.0 | 0.2 | 21.0 | 0.1 |
| 6 | 1.5312 | 8 | 20.0 | 0.2 | 20.8 | 0.3 |
| 7 | 1.5213 | 6 | 20.0 | 0.2 | 20.5 | 0.2 |
| 8 | 1.5422 | 14 | 20.0 | 0.2 | 20.8 | 0.3 |
| 9 | 1.5332 | 7 | 20.0 | 0.2 | 21.2 | 0.3 |

*Standard deviation, of diopter measurement, n = 10.

What is claimed is:

1. A copolymer consisting of: 2-phenyl ethyl acrylate from 67% to 70% by weight of the copolymer; hydroxyethyl methacrylate from 27% to 30% by weight of the copolymer, a crosslinker and an ultraviolet light absorbing material, wherein the ultraviolet light absorbing material is from 1% to 5% by weight of the copolymer; and further wherein the copolymer has an Equilibrium Water Content of about 3% and a refractive index of at least 1.54 in the dry state.

2. The copolymer of claim 1, wherein the ultraviolet light absorbing material is selected from the group consisting of: beta-(4-benzotriazoyl-3-hydroxyphenoxy)ethyl acrylate, 4-(2-acryloxyethoxy)-2-hydroxybenzophenone, 4-methacryloxy-2-hydroxybenzophenone, 2-(2'-methacryloxy-5'-methylphenyl)benzotriazole, 2-(2'-hydroxy-5'-methacryloxy-ethylphenyl)-2H-benzotriazole, 2-[3'-tert-Butyl-2'hydroxy-5'-(3'-methacryloyloxypropyl)phenyl]-5-chlorobenzotriazole, 2-[3'-tert-Butyl-5'-(3-dimethylvinylsilypropoxy)-2'-hydroxyphenyl]-5-methoxybenzotriazole, 2-(3'-Allyl-2'-hydroxy-5'-methylphenyl)benzotriazole, 2-[3'-tert-Butyl-2'-hydroxy-5'-[3'-methacryloyloxypropoxy) phenyl]-5-methoxybenzotriazole and 2-[3'-tert-Butyl-2'-hydroxy-5'-(3'-methacryloyloxypropoxy)phenyl]-5-chlorobenzotriazole.

3. The copolymer of claim 1, wherein the copolymer has a glass transition temperature (Tg) of from about 2° C. to about 20° C.

4. The copolymer of claim 1, wherein upon hydration the copolymer exhibits a change in diopter of less than 1.0 diopter for a 20 diopter lens.

* * * * *